(12) United States Patent
Chastain

(10) Patent No.: US 9,662,192 B2
(45) Date of Patent: May 30, 2017

(54) ORAL APPLIANCE CLEANING AND STORAGE DEVICE

(71) Applicant: Robert H. Chastain, Duluth, GA (US)

(72) Inventor: Robert H. Chastain, Duluth, GA (US)

(*) Notice: Subject to any disclaimer, the term of this patent is extended or adjusted under 35 U.S.C. 154(b) by 369 days.

(21) Appl. No.: 14/332,810

(22) Filed: Jul. 16, 2014

(65) Prior Publication Data

US 2015/0021211 A1 Jan. 22, 2015

Related U.S. Application Data

(60) Provisional application No. 61/846,797, filed on Jul. 16, 2013.

(51) Int. Cl.
*A61C 19/02* (2006.01)
*A63B 71/00* (2006.01)
*A61C 19/00* (2006.01)
*A63B 71/08* (2006.01)

(52) U.S. Cl.
CPC .......... *A61C 19/02* (2013.01); *A63B 71/0036* (2013.01); *A61C 19/002* (2013.01); *A63B 71/085* (2013.01)

(58) Field of Classification Search
CPC .... A61C 19/02; A61C 19/002; A63B 71/0036
USPC .................................................. 206/63.5
See application file for complete search history.

(56) References Cited

U.S. PATENT DOCUMENTS

| | | | |
|---|---|---|---|
| 4,783,056 A | | 11/1988 | Abrams |
| 5,383,745 A | * | 1/1995 | Shannon ........................ 405/52 |
| 6,343,612 B1 | * | 2/2002 | Dahl ............................. 134/117 |
| D545,066 S | * | 6/2007 | Bustos ........................... D4/199 |
| 2011/0308973 A1 | * | 12/2011 | Patenaude ..................... 206/63.5 |
| 2012/0181192 A1 | * | 7/2012 | Prewitt ......................... 206/63.5 |

OTHER PUBLICATIONS

Photograph of Sea Bond Denture Bath product, photograph taken Oct. 16, 2014.
Sea Bond website, accessed Mar. 10, 2015, <http://www.seabond.com/dental-bath/>.

* cited by examiner

*Primary Examiner* — Anthony Stashick
*Assistant Examiner* — Raven Collins
(74) *Attorney, Agent, or Firm* — Gardner Groff Greenwald & Villanueva, P.C.

(57) ABSTRACT

An oral appliance cleaning and storage device includes a housing, a top cap, and a bottom cap. The housing includes a first/wet compartment configured for receiving an oral appliance and a second/dry compartment configured for receiving at least one cleaner, breath mint, or other accessory.

18 Claims, 4 Drawing Sheets

ORAL APPLIANCE CLEANING AND STORAGE DEVICE

CROSS-REFERENCE TO RELATED APPLICATION

This application claims the benefit of U.S. Provisional Patent Application Ser. No. 61/846,797, filed Jul. 16, 2013, the entirety of which is hereby incorporated by reference.

TECHNICAL FIELD

The present invention relates generally to the field of oral appliances, and more particularly to a cleaning and storage device for oral appliances such as orthodontic retainers, dentures, mouth guards, etc.

BACKGROUND OF THE INVENTION

Users of all types of oral appliances such as orthodontic retainers, invisible braces, athletic mouth guards, night guards, sleep apnea devices, dentures, bridges, partial dentures and other removable oral appliances must clean their oral appliances regularly in order to avoid gum disease and other illnesses attributable to contamination by germs, dirt, decaying food and residue that can build up on oral appliances during and between uses. Users sometimes avoid cleaning, soaking, rinsing and/or wearing their oral appliances due to inconvenience, lack of time, lack of tools or because of an aversion to touching and handling their oral appliance as part of the cleaning process. Some youth and adolescents, as well as some adults, are embarrassed for others to see them handle and clean their oral appliance and therefore avoid proper care and usage of their appliance when traveling, visiting or when sharing a room with another person.

Thus, there is a need for an apparatus to speed and simplify the tasks of cleaning, soaking, rinsing, drying, storing and transporting oral appliances—while minimizing the amount of handling required and minimizing the number of tools associated with such tasks. There is also a need for an apparatus that enables even a lazy user to easily comply with the oral appliance care and usage instructions provided by the user's dental professional. Accordingly, it can be seen that needs exist for a discrete, integrated, compact and appealingly-designed apparatus for care and transport of an oral appliance that even adolescent users will not be embarrassed to use in the presence of another person. It is to the provision of an oral appliance cleaning and storage device meeting these and other needs that the present invention is primarily directed.

SUMMARY OF THE INVENTION

In example embodiments, the present invention relates to an oral appliance cleaning and storage device. In example forms, the oral appliance cleaning and storage device includes a housing or main body, a first closure member, and a second closure member. In example forms, the housing is generally cylindrical and includes a first compartment and a second compartment. The first compartment is generally configured to include impermeable walls and a perforated bottom or floor, and the second compartment is generally configured to include at least partially perforated walls and an impermeable or solid floor.

In one aspect, the present invention relates to an oral appliance cleaning and storage device including a housing, a top cap and a bottom cap. The housing extends from a first end to a second end and is generally cylindrical in shape. A first and a second compartment are defined within the housing. The first and second compartments are generally separated by a divider wall. The first compartment includes generally impermeable sidewalls and a perforated floor, and the second compartment includes at least one opening formed within a sidewall thereof and an impermeable floor. The top cap is provided for removable engagement with the first end of the housing, and the bottom cap is provided for removable engagement with the second end of the housing. Preferably, the first and second ends of the housing include threads.

In another aspect, the present invention relates to an oral appliance storage device including a housing, a top cap, and a bottom cap. The housing extends from a first end to a second end and includes a divider wall formed therein. The divider wall generally separates an internal portion of the housing into a first compartment and a second compartment. The top cap is provided for removable engagement with the first end and the bottom cap is provided for removable engagement with the second end of the housing. In example forms, the housing is generally cylindrical in shape. In one form, the first and second ends of the housing include interengagement features and the top and bottom caps include interengagement features, whereby the interengagement features of the first end provide interengagement with the interengagement features of the top cap, and whereby the interengagement features of the second end provide interengagement with the interengagement features of the bottom cap. The divider wall is generally impermeable and extends from the first end of the housing to the second end of the housing.

In yet another aspect, the present invention relates to a method of using a storage and cleaning device including the steps of: providing the housing, the second compartment including at least one cleaner therein; removably coupling the bottom cap to the second end of the housing; placing an oral appliance within the first compartment; removing one of the at least one cleaner from the second compartment and placing the cleaner in the first compartment; filling the first compartment with a liquid; removably coupling the top cap to the first end of the housing; draining the liquid from the first compartment, the liquid moving through one or more of the openings of the top cap that are in communication with the first compartment; removing the top and bottom caps from coupling engagement with the first and second ends of the housing; rinsing the appliance by providing a flow of liquid within the first compartment, in contact with the appliance, and through the perforated floor; removably coupling the top cap to the first end of the housing; air drying the appliance, the moisture being substantially removed through the openings formed within the floor of the first compartment; removably coupling the bottom cap to the second end of the housing; and transporting the device, the oral appliance being contained within the first compartment.

In another aspect, the present invention relates to a method of using a storage device including the steps of: providing the housing; removably coupling the bottom cap to the second end of the housing; placing an oral appliance within the first compartment; removably coupling the top cap to the first end of the housing; and transporting the device, the oral appliance being contained within the first compartment.

These and other aspects, features and advantages of the invention will be understood with reference to the drawing figures and detailed description herein, and will be realized by means of the various elements and combinations particularly pointed out in the appended claims. It is to be understood that both the foregoing general description and the following brief description of the drawings and detailed description of the invention are exemplary and explanatory of preferred embodiments of the invention, and are not restrictive of the invention, as claimed.

DETAILED DESCRIPTION OF EXAMPLE EMBODIMENTS

Figure 1:
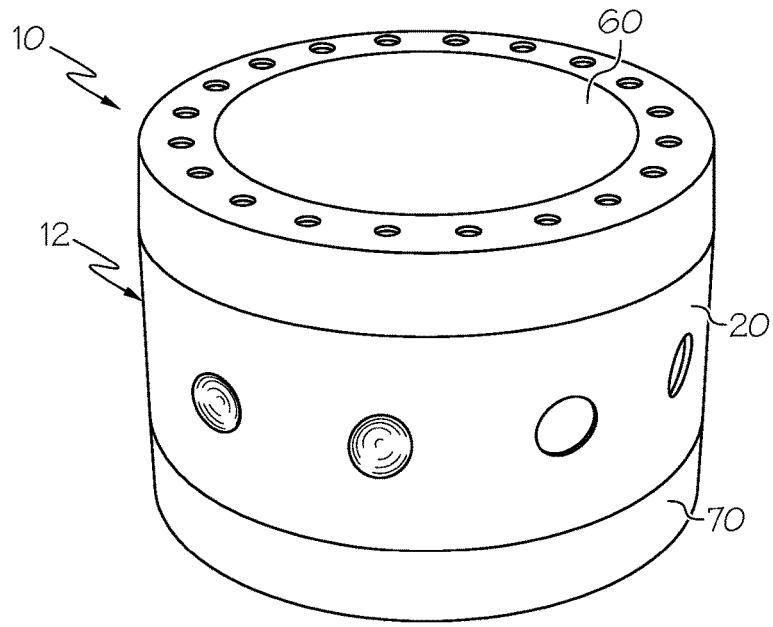
FIG. 1 is a perspective view of an oral appliance cleaning and storage device according to an example embodiment of the present invention.

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Any and all patents and other publications identified in this specification are incorporated by reference as though fully set forth herein.

Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

With reference now to the drawing figures, wherein like reference numbers represent corresponding parts throughout the several views, FIGS. 1-7 show an oral appliance cleaning and storage device 10 according to an example embodiment of the present invention. Generally, the cleaning and storage device 10 provides a convenient, compact, integrated, appealingly-designed and sanitary means by which to accomplish the tasks of cleaning, soaking, rinsing, drying, storing and transporting an oral appliance—while minimizing the number of tools and steps involved and minimizing the need for handling the oral appliance to complete each task. The device's 10 innovative, integrated, and visually-appealing design enables a user to easily, quickly and discretely comply with the oral appliance care and usage instructions provided by the user's dental professional with a minimum number of tools and with a minimum potential embarrassment. In most example forms, the device 10 is configured for use with oral appliances in the form of orthodontic retainers, invisible braces, athletic mouth guards, night guards, sleep apnea devices, dentures, bridges, partial dentures and other removable oral appliances.

Figure 2:
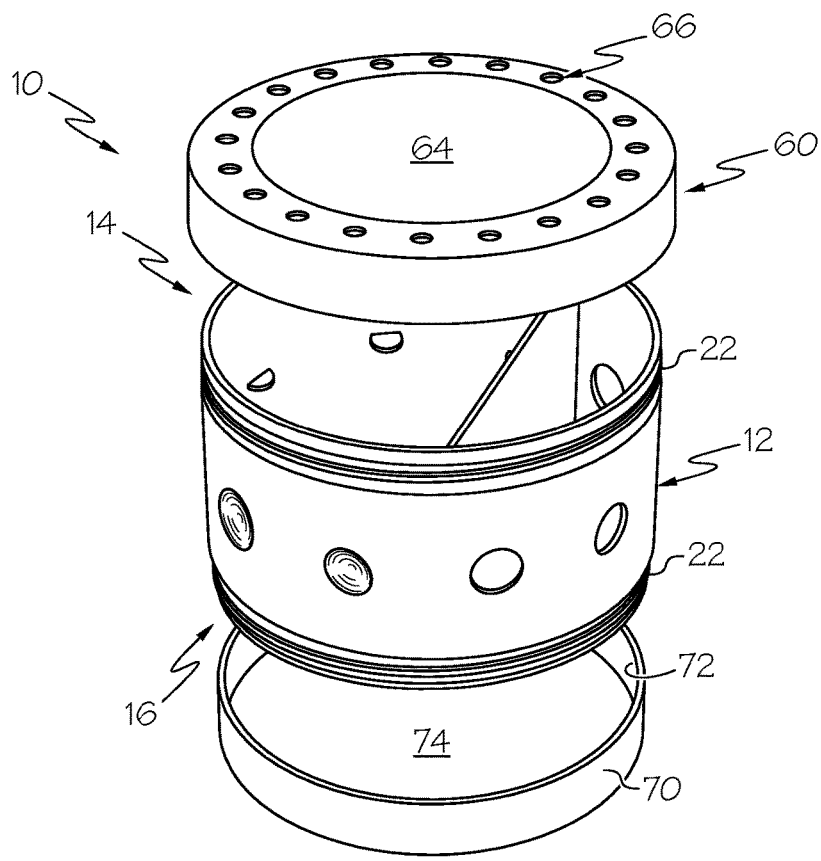
FIG. 2 is an exploded perspective view of the oral appliance cleaning and storage device of FIG. 1.

FIGS. 1-2 show the device 10 in an assembled state and an exploded state, respectively. Generally, the device 10 comprises a main body or housing member 12 defining an interior space, a first/top cap or closure member 60, and a second/bottom cap or closure member 70. The caps 60, 70 are removably coupled to the body 12 so that they can be repositioned between closed positions coupled to the body to prevent access to its interior and open positions removed (at least partially) from the body to permit access to its interior.

In one example form, the housing 12 is generally cylindrical in shape and comprises a generally cylindrical outer periphery 20. Preferably, the first and second caps 60, 70 generally comprise a complementary cylindrical shape such that the caps 60, 70 can removably couple to the ends of the housing 12. For example, in one form, a top end 14 of the housing comprises threads 22 for removably engaging mating threads 62 (unshown) of the top cap 60, and the bottom end 16 of the housing comprises threads 22 for removably engaging mating threads 72 of the bottom cap 70 (see FIG. 2). In other example embodiments, the caps 60, 70 can be in the form of a snap-on, slide-on, or hinged flip-type cap. Optionally, other engagement features or configurations may be provided as desired to removably couple the caps 60, 70 to the ends 14, 16 of the housing 12. Further optionally, the caps 60, 70 can removably couple to sides of the body instead of the top and bottom. Furthermore, the shape of the housing 12 and the caps 60, 70 can be configured as desired, for example, box-like, triangular, oval, spherical, D-shaped, or other shapes as desired. Preferably, in most example embodiments, the caps 60, 70 are generally complementary in shape to the shape of the housing 12.

Figure 3:
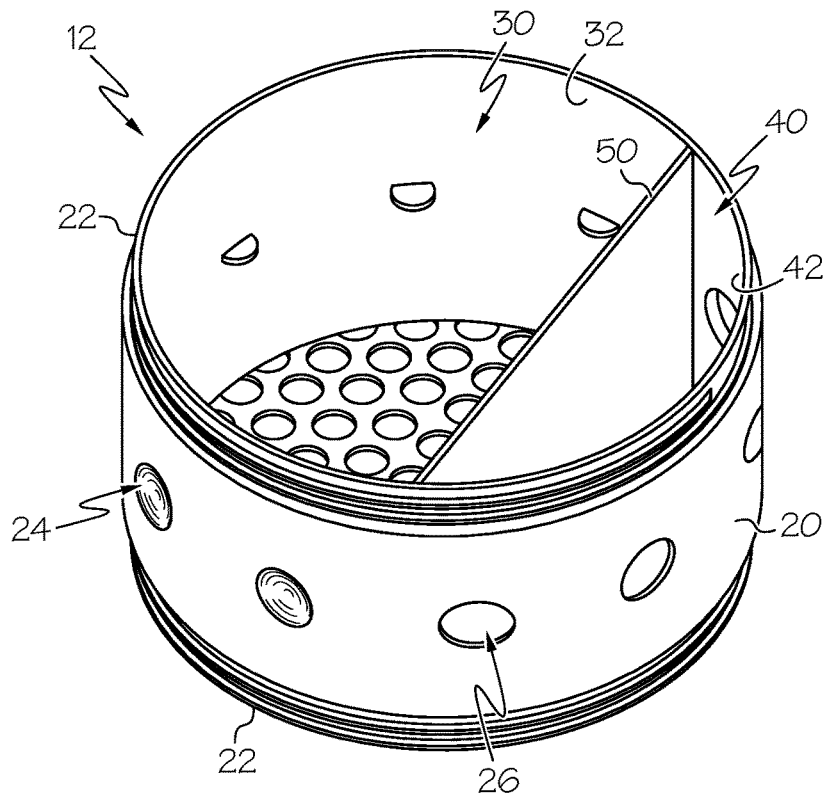
FIG. 3 is a perspective view of the main body of the oral appliance cleaning and storage device of FIG. 1, without its bottom and top.
Figure 4:
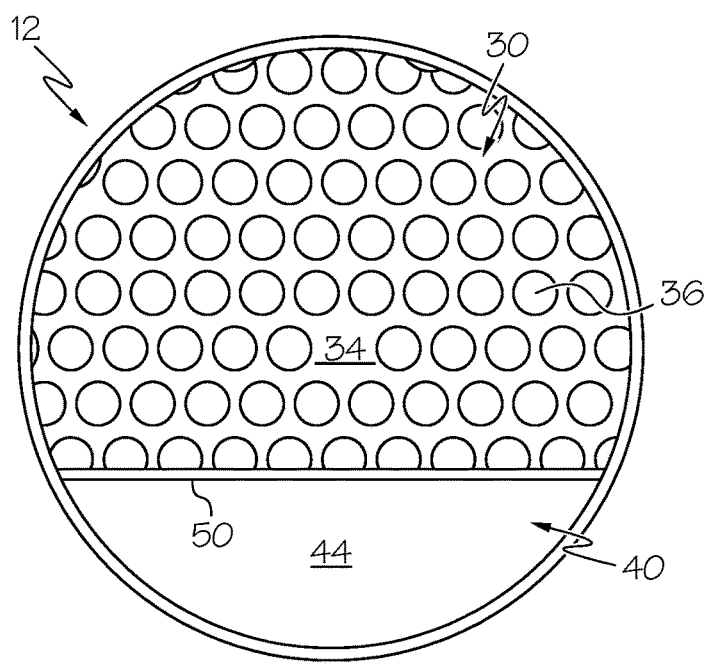
FIG. 4 is a top view of the main body of FIG. 3.
Figure 5:
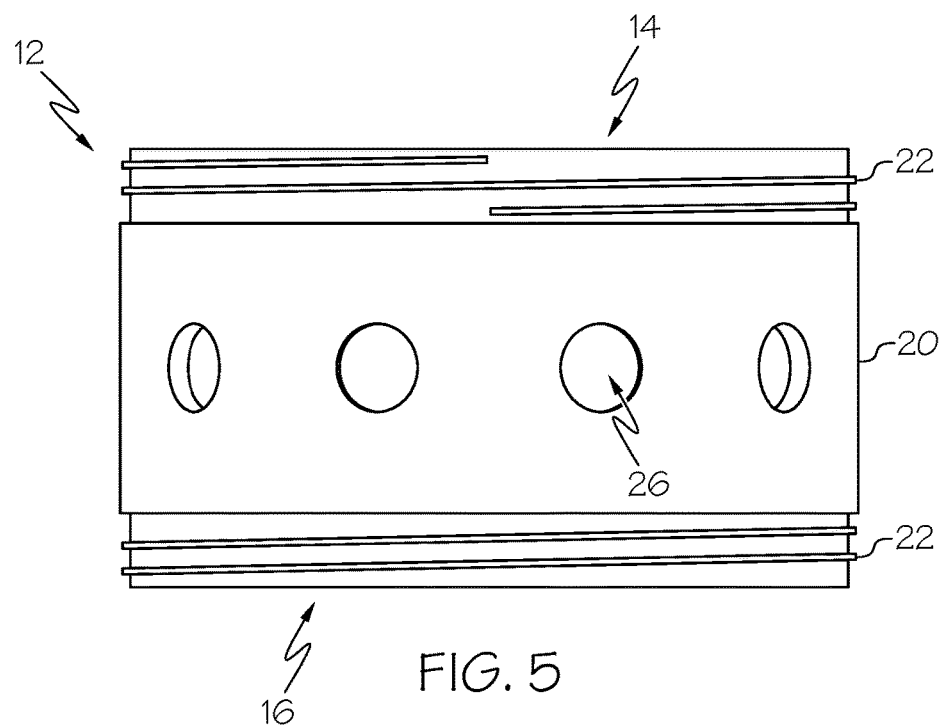
FIG. 5 is a side view of the main body of FIG. 3.

FIGS. 3-5 show the housing 12 in greater detail. As depicted, the housing 12 defines two or more compartments or divisions formed therein, for example, a first compartment ("wet compartment") 30 and a second compartment ("dry compartment") 40. Generally, the compartments 30, 40 are formed by first and second sidewall portions divided or separated by a divider or wall 50, which is typically offset from the center of the housing 12 such that the first compartment 30 is substantially larger than the second compartment 40. The divider wall 50 can be generally flat and linear as depicted, or it can include a bend (e.g., 90 degrees) to form a wedge-shaped dry compartment 40. Optionally, the divider wall can be generally U-shaped to define a generally U-shaped wet compartment and a slot-like dry compartment. In example forms as will be described below, the first compartment 30 is preferably sized to receive an oral appliance A (see FIG. 6) and the second compartment 40 is sized to receive one or more cleaners, for example, individually-wrapped effervescent cleaning tablet packets or other items such as breath-freshening mints. Typically, in most example embodiments, the divider 50 is generally solid and impermeable such that a liquid or other articles cannot pass between the first and second compartments 30, 40. In other embodiments, the compartments 30, 40 are of comparable size.

In one example form, the first/wet compartment 30 generally comprises a solid wall 32 (a portion of the peripheral wall 20 in combination with the divider 50) and a perforated bottom or floor 34. In one form, the bottom floor 34 comprises an array-like configuration of circular drain openings 36, which extend therethrough and allow communication with the second cap 70 when it is attached thereto (see FIG. 6). Otherwise, the openings 36 allow communication therethrough from the top end 14 to the bottom end 16 of the housing 12. Optionally, the openings can be sized and shaped as desired, with the floor 34 generally shaped and sized to support the oral appliance A, for example such that the oral appliance A does not pass therethrough. Preferably, the outer periphery 20 of the wall surrounding the first compartment 30 comprises a plurality of finger indentations or surface features 24 to provide an area wherein the user can grasp to provide for removal of the caps 60, 70 therefrom.

The second/dry compartment 40, which is generally sized to be the remainder of the space defined within the housing 12 (e.g., left over from the first compartment 30), generally comprises a perforated wall 42 (the remainder portion of the peripheral wall 20 in combination with the "solid" divider wall 50) and a solid, impermeable bottom or floor 44. In example forms, the perforated wall 42 consists of a plurality of vent openings 26 formed along the outer periphery 20 of the wall surrounding the second compartment 40. Preferably, the divider 50 extends from the solid floor 44 to the first end 14 of the housing 12, for example, such that contents contained within the first compartment 30 cannot enter the second compartment 40 between the top cap 60 and the uppermost portion of the divider wall 50.

Referring back to FIG. 2, the top cap 60 generally comprises a perforated top 64 that comprises a plurality of vent openings 66. Typically, the openings 66 are oriented about the top 64 in a circular-like array generally near the outer periphery thereof, which a respective portion thereof are generally in communication with the first and second compartments 30, 40 when coupled to the housing 12. And, the bottom cap 70 generally comprises an impermeable or solid bottom 74. Optionally, the top cap 60 may be replaced with an impermeable cap similar to the bottom cap 70. Preferably, the top cap 60 (comprising the perforated top 64) allows the first compartment 30 to breathe, and allows the second compartment 40 to breathe (in combination with the openings 26).

In the depicted embodiment, the dry compartment includes vent openings in its top cap portion and its sidewall portion. In other embodiments, the dry-compartment vent openings are provided in only its top cap or sidewall portion. In the depicted embodiment, the dry compartment includes its solid floor portion and its bottom cap portion. In other embodiments, only one of these is provided, with the floor sealing and blocking liquid from entering the dry compartment from its bottom (as depicted) but the cap not configured to extend across the dry compartment at its bottom, or with the floor not extending into the dry compartment but the cap configured to seal and block liquid from entering the dry compartment from its bottom.

In the depicted embodiment, the wet compartment includes vent openings in its top cap portion only. In other embodiments, the wet-compartment vent openings are additionally or alternately provided in an upper portion of its sidewall portion, with a lower portion of its sidewall portion remaining generally liquid-impermeable to cooperate with the divider wall and the bottom cap to form a liquid container in which the appliance can be soaked for cleaning.

Figure 6:
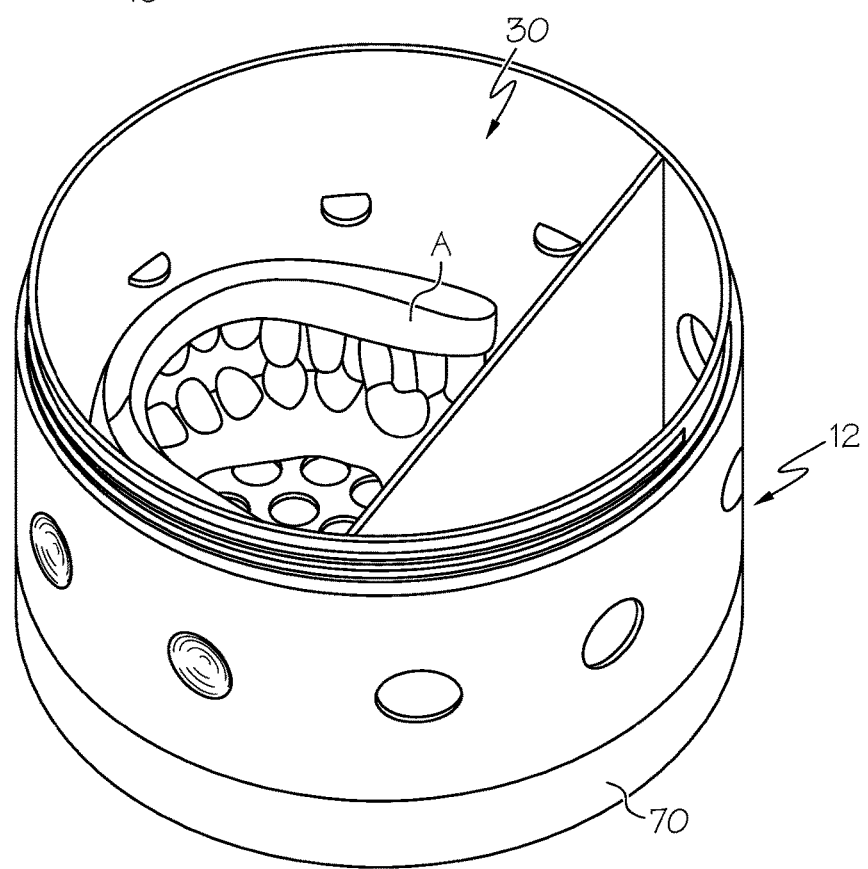
FIG. 6 is a perspective view of a portion of the oral appliance cleaning and storage device of FIG. 1, showing the top perforated cap removed and showing an oral appliance being positioned within a first compartment thereof.

In use, the device 10 preferably allows the user to clean, soak, rinse, dry, ventilate, store and transport the oral appliance A without every touching the oral appliance A itself. As depicted in FIG. 6, with the bottom cap 70 affixed to the second end 16 of the housing 12, the first compartment 30 can be filled with water for a soaking bath which can be used with liquid soap or effervescent cleaning tablets to clean and sanitize the oral appliance. Preferably, with the bottom cap 70 coupled to the second end 16 of the housing, any liquid or water contained within the first compartment 30 does not leak or otherwise escape from the second end 16, for example, due to the bottom cap 70 providing a water-tight seal. And, with the top cap 60 coupled to the first end 14 of the housing 12 (in combination with the bottom cap 70 coupled to the second end 16), openings 66 of the perforated top 64 allow the user to drain liquid from the first compartment 30 by simply tipping the device without opening either the top or bottom caps 60, 70 or handling the oral appliance A. This easy draining feature reduces the amount of handling so as to avoid contamination of the oral appliance A by dirty hands.

With the top and bottom caps 60, 70 removed from the housing 12, the perforated floor 34 of the first compartment 30 preferably securely contains the oral appliance A within the first compartment 30 to provide for thorough rinsing of the oral appliance A under a faucet or flow of water, with the water flowing across the oral appliance A and through the perforated floor 34 of the first compartment 30. This secure containment feature minimizes the risk that the oral appliance A will be dropped in a sink, down a drain or onto a contaminated surface such as a dirty floor or countertop. This easy rinsing feature reduces the amount of handling of the oral appliance so as to avoid contamination by dirty hands. After rinsing, the top cap 60 can be closed to securely contain the appliance A within the first compartment 30, with or without the bottom cap 70 being coupled thereto, which allows the appliance to air dry without having to remove it from the device 10. This easy air-drying feature also reduces the amount of handling so as to avoid contamination of the appliance by dirty hands. Once the oral appliance is completely dry and the bottom cap closed, the appliance can be stored or transported safely and securely. As described above, an impermeable top cap can be utilized as an option to completely seal the appliance against airborne dust contamination.

Figure 7:
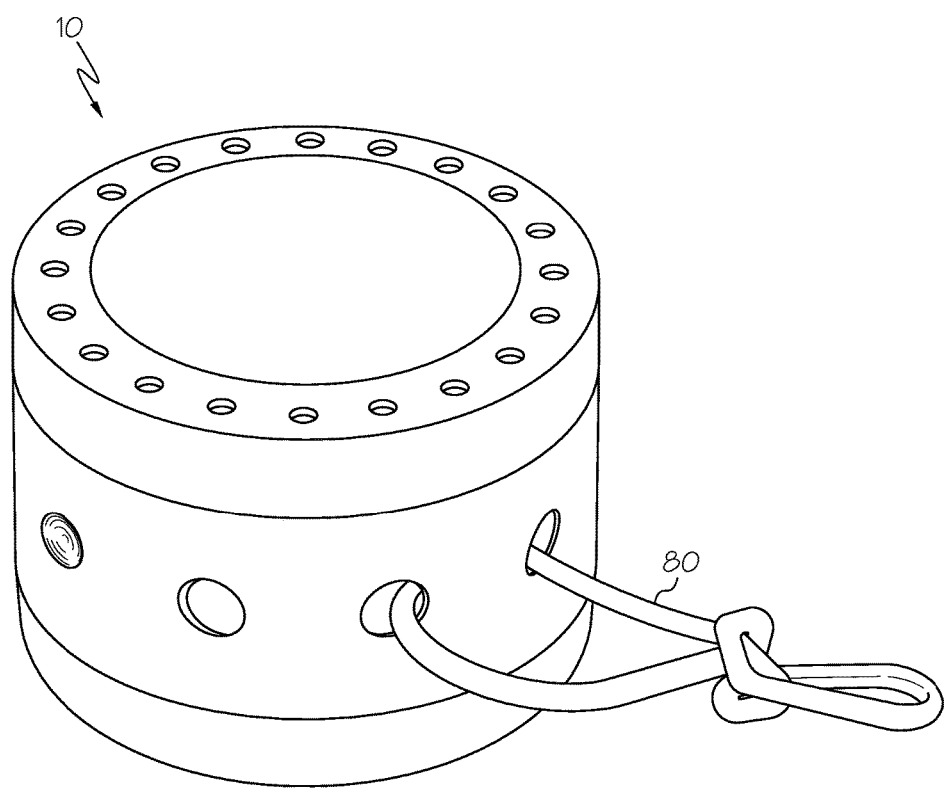
FIG. 7 is a perspective view of the oral appliance cleaning and storage device of FIG. 1, showing a lanyard attached to portions thereof for easy transporting.

As depicted in FIG. 7, the openings 26 of the second compartment 40 preferably allow the user to insert or attach a cord, tether or clip 80 for easy transporting of the device 10 either with or without the oral appliance A stored inside. Moreover, the perforated external wall or openings 26 of the second compartment 40 enables the user to visually distinguish the opposing internal location of the first compartment 30 to ensure that the user will intuitively know in which direction to tip the device 10 and drain the first compartment 30 while keeping the second compartment dry, all with the top cap 60 and impermeable bottom cap 70 closed and in place. The solid external wall of the first compartment 30 also helps to distinguish the opposing internal location of the second compartment 40. As described above, the solid external wall of the first compartment 30 comprises finger indentations 24 to help the user to grasp the housing 12 from any angle while removing or opening the top and bottom caps 60, 70.

In additional example embodiments, the present invention relates to a method of using the oral appliance cleaning and storage device 10. In one example form, the method comprises steps of providing the housing, the second compartment including at least one cleaner therein; removably coupling the bottom cap to the second end of the housing;

placing an oral appliance within the first compartment; removing one of the at least one cleaner from the second compartment and placing the cleaner in the first compartment; filling the first compartment with a liquid; removably coupling the top cap to the first end of the housing; draining the liquid from the first compartment, the liquid moving through one or more of the openings of the top cap that are in communication with the first compartment; removing the top and bottom caps from coupling engagement with the first and second ends of the housing; rinsing the appliance by providing a flow of liquid within the first compartment, in contact with the appliance, and through the perforated floor; removably coupling the top cap to the first end of the housing; air drying the appliance, the moisture being substantially removed through the openings formed within the floor of the first compartment; removably coupling the bottom cap to the second end of the housing; and transporting the device, the oral appliance being contained within the first compartment.

In another example form, the method comprises the steps of providing the housing; removably coupling the bottom cap to the second end of the housing; placing an oral appliance within the first compartment; removably coupling the top cap to the first end of the housing; and transporting the device, the oral appliance being contained within the first compartment.

While the invention has been described with reference to preferred and example embodiments, it will be understood by those skilled in the art that a variety of modifications, additions and deletions are within the scope of the invention, as defined by the following claims.

What is claimed is:

1. An oral appliance cleaning and storage device, comprising:
   a housing extending from a first end to a second end, the housing being generally cylindrical in shape and comprising a first and a second compartment defined therein, the first and second compartments being separated by a divider wall, the first compartment comprising generally impermeable sidewalls and a perforated floor, the second compartment comprising at least one opening formed within a sidewall thereof and an impermeable floor, the first and second ends comprising a plurality of threads;
   a top cap for removable engagement with the first end of the housing; and
   a bottom cap for removable engagement with the second end of the housing.

2. The oral appliance cleaning and storage device of claim 1, wherein the first compartment is substantially larger than the second compartment.

3. The oral appliance cleaning and storage device of claim 1, wherein the first compartment is configured for receiving an oral appliance.

4. The oral appliance cleaning and storage device of claim 1, wherein the second compartment is configured to receive one or more cleaners, individually-wrapped effervescent cleaning tablet packets or other items such as breath-freshening mints.

5. The oral appliance cleaning and storage device of claim 1, wherein the divider wall is generally solid and impermeable.

6. The oral appliance cleaning and storage device of claim 1, wherein the top cap comprises threads for removable engagement with the threads of the first end and a perforated top having a plurality of openings formed therein.

7. The oral appliance cleaning and storage device of claim 1, wherein the bottom cap comprises threads for removable engagement with the threads of the second end and an impermeable top.

8. The oral appliance cleaning and storage device of claim 1, wherein the oral appliance is in the form of orthodontic retainers, invisible braces, athletic mouth guards, night guards, sleep apnea devices, dentures, bridges, partial dentures and other removable oral appliances.

9. A method of use according to the storage and cleaning device of claim 1, the method comprising the steps of:
   providing the housing with the second compartment containing at least one cleaner therein;
   coupling the bottom cap to the second end of the housing;
   placing an oral appliance into the first compartment;
   removing one of the at least one cleaner from the second compartment and placing the cleaner into the first compartment;
   filling the first compartment with a liquid;
   coupling the top cap to the first end of the housing;
   draining the liquid from the first compartment, the liquid moving through one or more of the openings of the top cap that are in communication with the first compartment;
   removing the top and bottom caps from removable coupling engagement with the first and second ends of the housing;
   rinsing the appliance by providing a flow of liquid within the first compartment, in contact with the appliance, and through the perforated floor;
   coupling the top cap to the first end of the housing;
   air drying the appliance, the moisture being substantially removed through the openings formed within the floor of the first compartment;
   coupling the bottom cap to the second end of the housing; and
   transporting the device, the oral appliance being contained within the first compartment.

10. A device for storing an oral appliance and a cleaner, comprising:
    a housing including a peripheral sidewall extending from a first end to a second end, defining an interior, and having first and second sidewall portions, a divider wall positioned within the housing interior and separating the housing interior, in cooperation with the first and second portions of the peripheral sidewall, respectively, into a first wet compartment for storing the appliance and a second dry compartment for storing the cleaner, and a floor with a portion extending across the housing interior of the wet compartment;
    a top cap that removably engages the first end; and
    a bottom cap that removably engages the second end,
    wherein the wet compartment includes a plurality of drain openings for liquid drainage, the wet compartment includes a plurality of vent openings for drying, and at least lower portions of the divider wall and the wet-compartment portion of the peripheral wall are generally liquid-impermeable for liquid containment, and wherein the dry compartment includes a plurality of vent openings for drying.

11. The oral appliance storage device of claim 10, wherein the housing is generally cylindrical in shape.

12. The oral appliance storage device of claim 10, wherein the first and second ends of the housing each include interengagement features and the top and bottom caps each include interengagement features, wherein the interengagement features of the first end provide interengagement with the interengagement features of the top cap, and wherein the interengagement features of the second end provide interengagement with the interengagement features of the bottom cap.

13. The oral appliance storage device of claim 10, wherein the divider wall is generally impermeable and extends from the first end to the second end of the housing.

14. The oral appliance storage device of claim 10, wherein the wet-compartment drain openings are formed in the wet-compartment floor for liquid drainage.

15. The oral appliance storage device of claim 10, wherein a portion of the floor extends across the housing interior of the dry compartment, and the dry-compartment portion of the floor is liquid impermeable.

16. The oral appliance storage device of claim 10, wherein the bottom cap is generally liquid-impermeable for liquid containment.

17. The oral appliance storage device of claim 10, wherein the wet-compartment vent openings and the dry-compartment vent openings are formed in the top cap.

18. A method of use according to the storage device of claim 10, the method comprising the steps of:
   providing the housing;
   removably coupling the bottom cap to the second end of the housing;
   placing an oral appliance within the first compartment;
   removably coupling the top cap to the first end of the housing; and
   transporting the device, the oral appliance being contained within the first compartment.

* * * * *